United States Patent [19]

Bryant et al.

[11] Patent Number: 5,464,771
[45] Date of Patent: Nov. 7, 1995

[54] BIOLOGICALLY PURE CULTURE OF ACTINOMYCES VISCOSUS STRAIN USED FOR THE BIOREMEDIATION OF CHLORINATED HYDROCARBONS

[75] Inventors: Frank O. Bryant, Franklin Springs; Horace G. Cutler, Watkinsville, both of Ga.

[73] Assignee: The United States of America as represented by the Secretary of Agriculture, Washington, D.C.

[21] Appl. No.: 235,747

[22] Filed: Apr. 29, 1994

[51] Int. Cl.$^6$ .............................. C12S 13/00; C12N 1/20; C12N 1/38; C02F 3/00

[52] U.S. Cl. ..................... 435/262.5; 435/262; 435/244; 435/252.1; 210/601

[58] Field of Search ................................ 435/262, 262.5, 435/244, 252.1; 210/601

[56] References Cited

PUBLICATIONS

Bryant et al. Reductive Dechlorination of PCP by Actinomyces Viscosus strain Dechlorin. Abstr. Pap Am Chem Soc. 204th Mtg, Pt 1, ENVR 1 (1992).
Mohn et al., *Appl. Environ. Microbiol.*, 1992, 58, pp. 1367–1370.
Kuhn et al. *Soil. Sci. Soc. America*, 1989, 22, pp. 111–180.
Lamar et al., *Appl. Environ. Microbiol.*, 1990, 56, pp. 3093–3100.
Bryant et al., *Appl. Environ. Microbiol.*, 1991, 57, pp. 2293–2301.
Nicholson et al., *Appl. Environ. Microbiol.*, 1992, pp. 2280–2286.
DeWeerd et al., *Appl. Environ. Microbiol.*, 1991, 57, pp. 1929–1934.
Buchanon, et al Eds. Bergey's Manual of Determinative Bacteriology 8th ed., The Williams & Wilkins Co., 1974, pp. 657–681.
Gerhardt et al., eds. Manual Methods for General Bacteriology *American Society for Microbiology*, 1981, pp. 409–443.
Van Dort, et al., *Appl. Environ. Microbiol.*, 1991, 57, pp. 1576–1578.
Madsen et al., *Appl. Environ. Microbiol.*, 1992, 58, pp. 557–561.
De Marini et al., *Environ. Molec. Mutagen.*, 1990, vol. 15, pp. 1–9.

*Primary Examiner*—William H. Beisner
*Assistant Examiner*—T. J. Reardon
*Attorney, Agent, or Firm*—M. Howard Silverstein; John D. Fado; Joseph A. Lipovsky

[57] ABSTRACT

A strain of the bacterium *Actinomyces viscosus* ATCC-55473 has been discovered, which is able to reductively dechlorinate pentachlorophenol to lesser chlorinated products under anaerobic conditions without the formation of toxic intermediates. Compositions of the bacterium provide a methodology for bioremediation of chemically contaminated sites as an alternative to existing methods which are expensive and environmentally disruptive.

2 Claims, 4 Drawing Sheets

BIOLOGICALLY PURE CULTURE OF *ACTINOMYCES VISCOSUS* STRAIN USED FOR THE BIOREMEDIATION OF CHLORINATED HYDROCARBONS

BACKGROUND OF THE INVENTION

1. Field of the Invention

Concern for environmental safety requires the need to find methods in which to more effectively dispose of hazardous waste. This invention relates to a method for the enhanced biological remediation of chlorinated hydrocarbon pollutants. This is accomplished by inoculation of a contaminated substrate with a novel strain of *Actinomyces viscosus*.

2. Description of the Prior Art

Conventional techniques for remediation of toxic waste sites have focused on approaches utilizing excavation, filtration or immobilization. These techniques often do not include the transformation of the contaminants into innocuous products, but serve only to contain and/or concentrate the hazardous materials. By contrast, bioremediation techniques offer the potential to convert toxic contaminants into end products that are either less toxic or non-toxic. Bioremediation is hence developing as the method of choice over conventional remediation methods.

The U.S. Environmental Protection Agency (EPA) has invested heavily in research to develop bioremediation schemes for numerous toxic and mutagenic chemicals including chlorinated aromatic compounds. Homocyclic aryl chlorides, due to chlorination of the aromatic ring, are of low solubility and are thus recalcitrant to natural biodegradation. Research emphasis has consequently been placed on bioremediation schemes that dechlorinate the aromatic ring, thereby increasing compound solubility and exposure to microbiological degradation.

Pentachlorophenol (PCP) is a toxic and mutagenic chlorinated aromatic compound that is still routinely used as a biocide for wood preservation in the United States. Outside the U.S. PCP use is even more widespread. Consequently, the U.S. EPA has classified PCP as a priority pollutant. Numerous bacteria have been isolated in culture that can biodegrade PCP and other chlorinated aromatic compounds under aerobic conditions, however, attempts to biodegrade PCP under anaerobic conditions, which prevail at toxic waste sites, can result in either no PCP removal (Mohn et al., *Appl. Environ. Microbiol.*, 1992, 58, pp. 1367–1370) or generation of pentachloroanisole as the main product (Kuhn et al., Soil Sci. Soc. America; 1989, 22, pp. 111–180; Lamar et al., *Appl. Environ. Microbiol.*, 1990, 56, pp. 3093–3100). Although pentachloroanisole is less toxic than PCP, it is more stable and thus less amenable to further biodegradation.

PCP biodegradation under anaerobic conditions proceeds predominantly by the mechanism of reductive dechlorination as the initial step. Reductive dechlorination involves a two electron transfer in which chlorine is removed as chloride (Cl−) from homocyclic aryl chlorides and replaced by a proton (H+) from water. Reductive dechlorination of chlorinated aromatic compounds by microbial consortia have been studied in sludges and sediments under methanogenic-type, anaerobic conditions (Bryant et al., *Appl. Environ. Microbiol.*, 1991, 57, pp. 2293–2301), however, a period of adaptation to the presence of chlorophenols is often required to establish effective rates of dechlorination Nicholson et al. (*Appl. Environ. Microbiol.*, 1992, 58, pp. 2280–2286) have published a summary of pathways of reductive dechlorination of chlorophenols by non-adapted and adapted microbial consortia.

One anaerobic bacterium isolated in pure culture, *Desulfomonile tiedjei* (DCB-1), removes chlorine and derives energy and carbon from 4-chlorobenzoic acid. Reductive dechlorination of 4-chlorobenzoic acid proceeds by reduction of the aromatic ring and the addition of a proton derived from water. DCB-1 also dechlorinates PCP at low concentrations (<3 µg/ml) but only as a detoxifying mechanism since neither energy or carbon is derived from PCP (Mohn et al., *Appl. Environ. Microbiol.*, 1992, 58, pp. 1367–1370). *Desulfomonile tiedjei*, taxonomically is a sulfate-reducer and the reduction of sulfate is preferred over dechlorination as a means of removing reducing equivalents (DeWeerd et al., *Appl. Environ. Microbiol.*, 1991, 57, pp. 1929–1934).

SUMMARY OF THE INVENTION

We have now discovered a new strain of the bacteria *Actinomyces viscosus* that is capable of the degradation of pentachlorophenol under anaerobic conditions without the production of toxic or mutagenic intermediates.

In accordance with this discovery, it is an object of this invention to provide a new bacterium that can be mass-produced and formulated for the biodegradation of PCP and other homocyclic chlorinated hydrocarbons under anaerobic conditions.

It is also an object of the invention to provide new mechanisms for the biodegradation of chlorinated phenols.

Another object of the invention is to provide a biological alternative to existing disposal methods of chlorinated phenols which presently include excavation, filtration, and immobilization.

Another object of this invention is to provide a means by which to produce innocuous intermediates from PCP.

Other objects and advantages of this invention will become readily apparent from the ensuing description.

DETAILED DESCRIPTION OF THE INVENTION

Figure 1A:
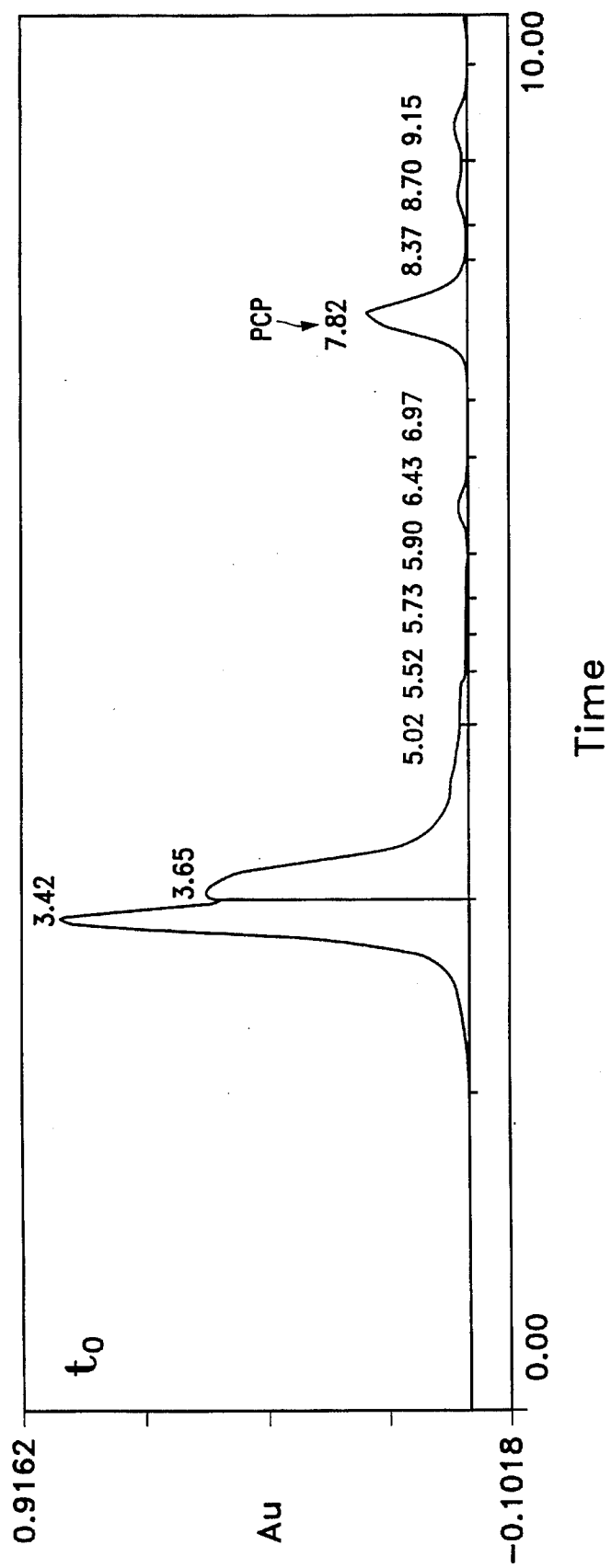
FIGS. 1a and 1b represent the high pressure liquid chromatograms of a contaminated sample of unflocked process water at the time of treatment with ATCC 55473 and 22 days later, respectively.

The strain of *Actinomyces viscosus* for use herein was isolated from a composition derived from dairy cow manure. This strain, which can be cultured in isolation, was found to be capable of anaerobically metabolizing homocyclic chlorinated hydrocarbons.

The bacterium of the invention, designated *Actinomyces viscosus dechlorini* was subjected to systematic tests, including procedures for the determination of special characteristics, performed in accordance with *Bergey's Manual of Systematic Bacteriology* (Gottlieb; 8th ed; The Williams and Wilkins Co., 1974, pp. 657–681) and the *Manual of Methods for General Bacteriology* (Smibert et al., American Society for Microbiology, 1981, pp. 409–443).

Specifically, the bacterium grew under anaerobic and aerobic conditions indicating that it was a facultative anaerobe. Microcolonies grew aerobically within 24 hours on potato dextrose agar (PDA) at 37° C. displaying a dense core and filamentous (spidery) appearance at the periphery. Liquid cultures initially displayed filamentous cells of various lengths and branching. As the culture grew, the filaments eventually fragmented into coccoid cells and finally formed mucoid aggregates that appeared as a flocculent mass in the medium. Consequently, the bacterium displayed pleomorphic growth. All tests for spores were negative although coccoid cells were refractile in appearance. The bacterium was indole negative, urease negative, gas production negative and catalase positive. The principle fermentation product was lactic acid but also acetic, succinic and formic acid were produced; propionic acid was not produced. All cell types were non motile. These findings are summarized below.

Characteristics of *Actinomyces viscosus* strain *dechlorini*

Facultative anaerobe

Pleomorphic: Filaments (early log phase), diphtheroid or chains of coccoids (mid to late log phase), coccoids and aggregates (late log and stationary phase). All cell types are non-motile.
Microcolonies: Dense core with filamentous (spidery) periphery, no pigments.
Liquid culture: Log phase cultures display heavy growth with a clear zone between liquid surface and ~1 cm depth into medium. Late log and stationary phase culture displays mucoid or papery cell aggregates.
Optimal growth temperature range: 20°–37° C.
Gram stain and Acid fast responses: positive
Spore tests: negative
Indole, urease and gas production: negative
Catalase activity: positive
Principle fermentation product from glucose: lactate
Secondary fermentation products: acetate, succinate and formate but NOT propinate.
Principle fatty acids: $C_{15}$ and $C_{17}$ The isolate has been deposited under the Budapest Treaty in the American Type Culture Collection (ATCC) at 12301 Parklawn Drive, Rockville, Md., 20852. U.S.A., on Sept. 16, 1993 under the name *Actinomyces viscosus, dechlorini* and has been assigned Accession Number ATCC 55473. For purposes of this invention, any isolate of this bacterium having all the identifying characteristics of ATCC 55473, including mutants of ATCC 55473 having the capability of the parent microorganism for degrading pentachlorophenol under anaerobic conditions without productions of toxigenic or mutagenic intermediates selected from the group consisting of 2,3,4,5-tetrachlorophenol; 2,3,4-trichlorophenol; 3,4,5-trichlolorphenol; 2,4,5-trichlorophenol; 2,4,6-tricholophenol and 2,3,6-trichlorophenol, would be effective.

The bacteria can be mass-produced and maintained for use by any conventional means: the preferred temperature range for growth is about 20° C. to about 37° C., and the pH should be in the range of about 5 to about 9, preferably about 7 to about 8. The bacteria is preferably incorporated into compositions appropriate for the desired applications by combining it with a suitable liquid vehicle or solid carrier. The actual concentration of ATCC 55473 in the formulated composition is not particularly critical and is a function of practical considerations such as the properties of the vehicle or carrier, the type of toxic substrate to be treated, and the method of application to the substrate. The biotransformation of homocyclic chlorinated hydrocarbons including PCP by the instant organism has an obligate requirement for an organic nitrogen source, such may be provided by the toxic substrate itself or from any compatible source in amounts sufficient to prevent its acting as a growth limiting factor. As a nitrogen source De yeast extract is preferred due to its potential possession of other components that may facilitate the bioremediation of homocyclic chlorinated hydrocarbons. While not requisite, enhanced capacity to biotransform greater concentrations of such toxins by Applicants' bacterium is achieved by the optional inclusion of lactic acid to the medium. Rates of inclusion are situationally dependent with the determination of optimally beneficial amounts being within the purview of the skilled artisan. For purposes of formulation and application, an "effective amount" is defined to mean any such quantity of Applicants organism or compositional adjuvant sufficient to detoxify the target substrate.

ATCC 55473 has the highly desirable ability to bioremediate homocyclic chlorinated hydrocarbons, including PCP under anaerobic conditions. These compounds may be represented by the structural formula:

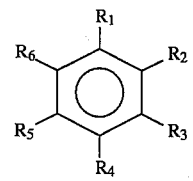

wherein:
  $R_1$ may be OH, Cl or O-alkyl and
  $R_2, R_3, R_4, R_5$ and R6 may each independently be H or Cl. This allows substrates located in oxygen deprived environments, where aerobes will not thrive, such as in drainage lagoons and dump or burial sites to be candidates for bioremediation. The substrates treated may be solid, liquid, aqueous, or mixtures thereof. Preservative-treated cellulosic wastes are particularly envisioned.

While not desiring to be bound by any particular theory of operation, organic acids apparently serve dually as electron donors to reduce chlorinated compounds, and as a carbon and energy source for the bacterium. PCP serves as an electron acceptor, apparently increasing available cellular energy for bacterial growth and replication. This suggests a co-catabolic relationship between DL-lactic acid and PCP indicative of a form of anaerobic respiration in *Actinomyces viscosus* sp. strain *dechlorini* (ATCC 55473). When grown on lactic acid and yeast extract under anaerobic conditions, the bacterium apparently follows the path of reductive dechlorination of PCP shown below:

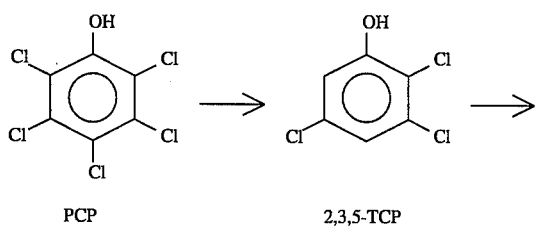

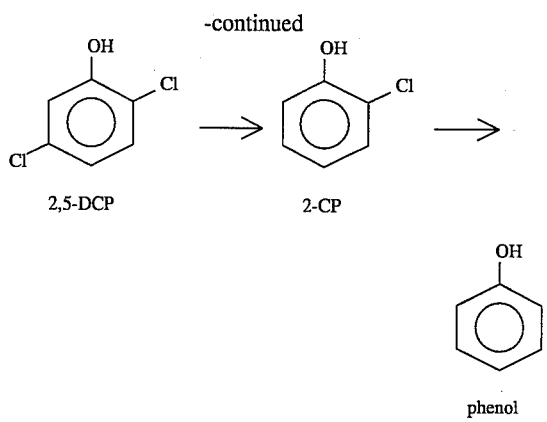

Recently, another group has observed that PCP is reduced to 2,3,5,6-tetrachlorophenol and then to 2,3,5-trichlorophenol by a methanogenic consortium adapted to PCP (Nicholson et al., *Appl. Environ. Microbiol.*, 1991, 57, pp. 1576–1578). However, this was subsequently reduced to 3,5-dichlorophenol rather than the 2,5-dichlorophenol which results from ATCC 55473. Significantly, Applicants bacterium does not generate 2,3,4,5-TeCP, 2,3,4-, 3,4,5-, 2,4,5-, 2,4,6-, or 2,3,6-TCP which have all been shown to be toxic (Madsen et al., *Appl. Environ. Microbiol.*, 1992, 58, pp. 557–561) and/or mutagenic (DeMarini et al., *Environ. Molec. Mutagen.*, 1990, 15, pp. 1–9). Of the six possible trichlorophenols that could be generated from PCP, the only one that lacks such negative associations 2,3,5-TCP, is produced by the bacterium. Consequently, biotransformation of PCP by this bacterium apparently avoids the production of toxic or mutagenic intermediates entirely.

The following examples are intended only to further illustrate the invention and are not to be construed as being of a limitative nature.

EXAMPLE 1

Biotransformation of PCP by *A. viscosus* strain *dechlorini*. Minimal medium for PCT biotransformation by *A. viscosus* strain *dechlorini*.

To maximize PCP biotransformation by *A. viscosus* strain *dechlorini*, the least complex medium was determined in which to culture the bacterium to facilitate the utilization of PCP as a carbon and/or energy source.

The medium of Table I was prepared under anaerobic conditions using the Hungate Technique (Smibert et al., *Manual of Methods for General Bacteriology*, American Society for Microbiology, 1981, pp. 409–443). The ingredients of the medium were combined and ~30 ml distributed into 50 ml serum-stoppered bottles. The serum-stoppered bottles were vented with disposable 23 gage syringe needles and autoclaved for 50 minutes at 15 psi. The serum-stoppered bottles were removed immediately after the autoclave cycles were complete and flushed with $N_2$ gas (>99%) for at least 10 minutes. The medium was used immediately upon cooling to room temperature. Inoculation was performed anaerobically with a syringe from a growing culture of the bacterium. PCP (10 µg/ml) was added with a syringe from a stock solution of 3000 µg/ml PCP in 50% aqueous methanol. The bacterium was unable to utilize methanol as a growth substrate.

TABLE I

| Ingredients | Quantities/liter |
| --- | --- |
| $KH_2PO_4$ | 1.5 g |
| $K_2PO_4$ | 1.5 g |
| $NH_4Cl$ | 0.5 g |
| $MgCl_2.6H_2O$ | 0.18 g |
| Yeast Extract (Difco) | 2.0 g |
| Reducing solution[a] | 40.0 ml |

[a]Reducing solution contained 200 ml of 0.2N NaOH plus 2.5 g $Na_2S.9H_2O$.

PCP (13 µg/ml) was biotransformed by a culture of *A. viscosus* strain *dechlorini* under anaerobic conditions at 37° C. during 24 hours growth on this medium of basic mineral salts and yeast extract (0.1%). Upon a second addition of PCP (52 µg/ml), PCP was removed to 5.5 µg/ml. Cell growth increased from $2 \times 10^6$ to $2 \times 10^8$ cell/ml as PCP was removed (TABLE II). No lag phase was associated with PCP removal.

TABLE II

| TIME (hrs) | CELLS/ml × $10^7$ | PCP (ug/ml) |
| --- | --- | --- |
| 0 | 3.0 | 13 |
| 18 | 3.2 | 7.5 |
| 24 (spike) | 4.9 | 0/52 |
| 42 | 6.0 | 44 |
| 66 | 12.0 | 14.5 |
| 114 | 20.0 | 6.0 |

PCP (99%) was obtained from Aldrich Chemical Co. A stock solution of PCP (3000 µg/ml) in 50% aqueous methanol was used to supply PCP to cell cultures and controls. Methanol was not utilized as a growth substrate by the bacterium. PCP was identified and quantified by HPLC analysis and cochromatography with a PCP standard in 50% aqueous methanol. The HPLC system consisted of an LDC ConstaMetric 4100 solvent delivery system, a LDC SpectroMetric 5000 photodiode array monitor selected at 290 nm, a Gateway 2000 computer equipped with LDC software package and an Epson LX-810 recorder. The column was a nucleosil C18 5U reverse-phase (250×4.6 mm). The mobile phase was ethanol:water:glacial acetic acid (80:19:1). Cell growth was monitored by direct cell count using an Improved Neubauer Ultra Plane counting chamber (1/400 sq. mm×1/10 mm) an Olympus BH2 phase contrast microscope.

Upon transfer of the bacterium to fresh medium identical to that of Table I with the exception that yeast extract was excluded, PCP (12 µg/ml) was biotransformed at a slower rate requiring 13 days for removal at 37° C. Growth of the bacterium as shown in Table III increased from $10^6$ to $10^9$ cell/ml as PCP was removed.

TABLE III

| TIME (days) | CELLS/ml × $10^7$ | PCP (control) | PCP (ug/ml) |
| --- | --- | --- | --- |
| 0 | 0 | 11.5 | 12.0 |
| 2 | 4.7 | 11.5 | 7.0 |
| 5 | 16.0 | 11.5 | 3.0 |
| 7 | 20.0 | 11.0 | 1.5 |
| 13 | 50.0 | 10.5 | 0 |
| 21 | 80.0 | 11.0 | 0 |

Although the rate of PCP biodegradation was lower than in Table II, no lag phase was apparent and the final concentration of cells was higher. Both cultures actively biotransformed PCP and accumulated 2,4,5-trichlorophenol (TCP) as determined by comparison to standards. Tetrachlorophenols (TeCP) were not detected. Determination of lesser chlorinated intermediates was not performed.

The observed difference in rate of PCP removal between Table II and Table III is likely the result of added yeast extract since this is the only difference in the media. The culture described in Table III was limited to the yeast extract obtained in the inoculum from the culture in Table II. A subsequent attempt to obtain growth and PCP biotransformation without yeast extract in the medium using the culture of Table III as inoculum, displayed little cell growth or PCP biotransformation. Several concentrations of glucose in the minimal medium promoted excellent growth of the bacterium but PCP was either not removed or removed slowly when added to glucose-containing media. Autoclaved control cultures were maintained for each active culture. Controls did not remove PCP, accumulate intermediates or demonstrate cell replication.

EXAMPLE 2

Enhanced PCP biotransformation by A. viscosus strain dechlorini with DL-lactic acid supplementation.

In order to enhance biotransformation of PCP at concentrations above 100 μg/ml by A. viscosus strain dechlorini, the basic mineral salts medium containing yeast extract (0.1%) was supplemented with various metal salts and volatile fatty acids. As shown in Table IV, supplementation of the medium with DL-lactic acid, biotransformed PCP at an initial concentration of 126 μg/ml at 22° C. As PCP was biotransformed between days 0 to 5, cell replication increased logarithmically to $2.5 \times 10^8$ cells/ml. A subsequent addition of DL-lactic acid (0.17%) on day 9 resulted in a second phase of logarithmic cell growth to $>10^9$ cells/ml. During the time-course chlorinated intermediates including 2,3,5-TCP, 2,5-dichlorophenol (DCP) and 2-chlorophenol (CP) were produced. Biotransformation of PCP at concentrations above 100 μg/ml by the bacterium without DL-lactic acid supplementation, either did not occur or was sufficiently slow that intermediates were not produced.

TABLE IV

| TIME (days) | CELLS/ml × 10⁷ | PCP | 2,3,5-TCP | 5-2,DCP | 2-CP |
|---|---|---|---|---|---|
| 0 | 0.0 | 125 | 0 | 0 | 0 |
| 1 | 8.0 | 113 | 0 | 0 | 0 |
| 4 | 20.0 | 104 | 0 | 1.2 | 19.4 |
| 5 | 24.0 | 90 | 0 | 4.3 | 18.4 |
| 7 | 24.0 | 89 | 0 | 3.8 | 25.0 |
| 9 | 24.0 | 74 | 1.4 | 2.5 | 20.6 |
| 11 | 40.0 | 69 | 9.6 | 38.0 | 25.4 |
| 12 | 100.0 | 44 | 1.8 | 21.0 | 53.0 |
| 16 | 100.0 | 49 | 2.0 | 19.0 | 52.0 |
| 21 | 100.0 | 43 | 2.0 | 19.0 | 48.0 |

Progress of biotransformation of PCP and product formation in a medium of basic mineral salts, 0.1% yeast extract and 0.05% DL-lactic acid (85%) with a subsequent addition of DL-lactic acid (0.17%) on day 9. The inoculum (0.3 ml) was from the active culture of TABLE III. Cell concentrations on days 11, 12, 16 and were ~10⁹ cells/mi. PCP and 2,3,5-TCP were identified and quantified as described in TABLE II. 2,5-DCP and 2-CP were identified and quantified as described in TABLE II, except that the mobile phase was acetonitrile:water:glacial acetic acid (50:48:2) and the photodiode array monitor was selected at 280 nm. A chlorinated phenol kit from Ultra Scientific containing all chlorophenol congeners was obtained for cochromatography to identify and quantify intermediates from reductive dechlorination of PCP. Cell growth was as determined in TABLE II.

Progress of cell replication at 22° C. of A. viscosus strain dechlorini grown in the presence of PCP compared to a culture of the bacterium grown on the same medium but without PCP is shown in Table V. The cultures were inoculated and monitored coincidentally. A higher rate of cell replication was observed in the culture containing PCP until day 13 when both cultures reached a concentration of $6 \times 10^8$ cells/ml. Upon a second addition of DL-lactic acid on day 13, a higher rate of cell replication was again observed in the culture containing PCP until day 19 when both cultures reached concentration of $1.2 \times 10^9$ cell/ml. Both cultures demonstrated cell aggregation beyond day 19 making accurate cell counts difficult.

TABLE V

| | CELLS/ml × 10⁷ | |
|---|---|---|
| TIME (days) | +PCP | -PCP |
| 0 | 0 | 0 |
| 1 | 16.0 | 20 |
| 6 | 60.0 | 40.0 |
| 13 | 60.0 | 60.0 |
| 14 | 62.0 | 60.0 |
| 15 | 78.0 | 65.0 |
| 19 | 120.0 | 120.0 |

Progress of cell replication was monitored as described in TABLE II. The bacterium was grown on minimal media containing yeast extract (0.1%) (but not glucose) with additions of DL-lactic acid on day 0 (0.1%) and on day 13 (0.16%). PCP additions were on day 0 (26 μg/ml) on day 15 (123 μg/ml). A separate culture was monitored for cell replication to which PCP was never added. The inoculum was 0.1 ml of the culture actively biotransforming PCP described in TABLE IV.

The progress of biotransformation of PCP and product formation by the A. viscosus strain dechlorini of Table V is shown in Table VI. Similar to Table V, the addition of DL-lactic acid on day 13 was coincident with an increase in the rate of biotransformation of PCP (19 to 1μg/ml). A subsequent addition of PCP on day 15 was biotransformed at a similar rate by day 19 (123 to 71 μg/ml) when further removal of PCP ceased. DL-lactic acid (0.16%) was again added on day 21 but an increase in the rate of PCP biotransformation was not observed until between day 28 and 41 (74 to 8 μg/ml). Since the final addition of DL-lactic acid was not coincident with an increase in the rate of PCP biotransformation and since a dependence on yeast extract was previously noted, additions of yeast extract were made on days 39 (0.1%) and 43 (0.1%). Coincident with yeast extract addition was an increase in the biotransformation to 2,3,5-TCP between days 39 and 41 (75 to 10 μg/ml) and, subsequently, 2-CP between days 41 and 43 (64 to 1μg/ml). Phenol was observed by day 39 coincident with accumulation of 2,3,5-TCP and 2-CP. An autoclaved culture was monitored as a control. PCP was not biotransformed nor were chlorinated intermediates formed in the control.

TABLE VI

| TIME/days) | | PCP | 2,3,5-TCP | 2,5-DCP | 2-CP | PHENOL |
|---|---|---|---|---|---|---|
| | 0 | 26.0 | 0 | 0 | 0 | 0 |
| | 1 | 22.5 | 0 | 0 | 0 | 0 |
| | 6 | 21.7 | 0 | 0 | 0 | 0 |
| | 13 | 19.8 | 0 | 0 | 0 | 0 |
| | 14 | 1.5 | 5.5 | 14.8 | 0 | 0 |
| | 15 | 1.1 | 10.4 | 18.0 | 0 | 0 |
| Spike | 15 | 123.5 | 10.4 | 18.0 | 0 | 0 |
| | 16 | 104.3 | 23.4 | 24.0 | 0 | 0 |
| | 19 | 70.9 | 5.5 | 24.8 | 0 | 0 |
| | 21 | 71.6 | 7.8 | 6.3 | 17.0 | 0 |
| | 22 | 80.0 | 7.8 | 6.3 | 20.4 | 0 |
| | 25 | 84.0 | 7.8 | 5.8 | 12.6 | 0 |
| | 28 | 68.9 | 8.2 | 7.4 | 16.0 | 0 |
| | 39 | 14.4 | 75.0 | 0.0 | 46.0 | 12.1 |
| | 41 | 8.0 | 10.0 | 5.2 | 64.0 | 23.4 |
| | 43 | 8.8 | 10.6 | 4.6 | 0.0 | 16.1 |
| | 46 | 0.3 | 11.4 | 5.2 | 6.1 | 20.8 |

Progress of biotransformation of PCP and product formation by the *A. viscosus* sp. strain *dechlorini* culture described in TABLE V. Further additions were made of DL-lactic acid on day 21 (0.16%) and of yeast extract on days 39 (0.1%) and 43 (0.1%). PCP and products were identified and quantified as described in TABLES II and IV. An autoclaved culture was maintained as a control. PCP was not removed nor were chlorinated intermediates produced in the control.

EXAMPLE 3

Biotransformation of PCP-Containing Aqueous Samples Laboratory scale biotransformation of PCP-containing aqueous samples.

On site samples were obtained from a wood treatment facility. The samples included unflocked process water and flocked process water in which PCP was the major aromatic contaminant. Phenanthrene, fluoranthrene, n-docosane, n-tetracosane, pyrene and hexanoic acid were also present in the process water. Also, a sample of groundwater from the site contained PCP and numerous other halogenated and aromatic compounds including nitrosopyrrolidine, pentchlorobenzene, nitrophenol, dibenzofuran, fluroanthene, fluorene, nitrobenzene, nitroaniline, nitrosopiperidine, toxaphene, PCBs, 2,4-D and 2,4,5-T as major contaminants as determined by an independent laboratory. Aliquots (30 ml) of each sample were transferred to separate 50-ml serum-stoppered bottles, autoclaved for 20 minutes at 15 psi and degassed with $N_2$ to obtain anoxic conditions. All samples were made to 0.5% DL-lactic acid. One bottle from each sample source was inoculated with *A. viscosus* strain *dechlorini*. A non-inoculated control was maintained from each sample source.

Figure 1B:
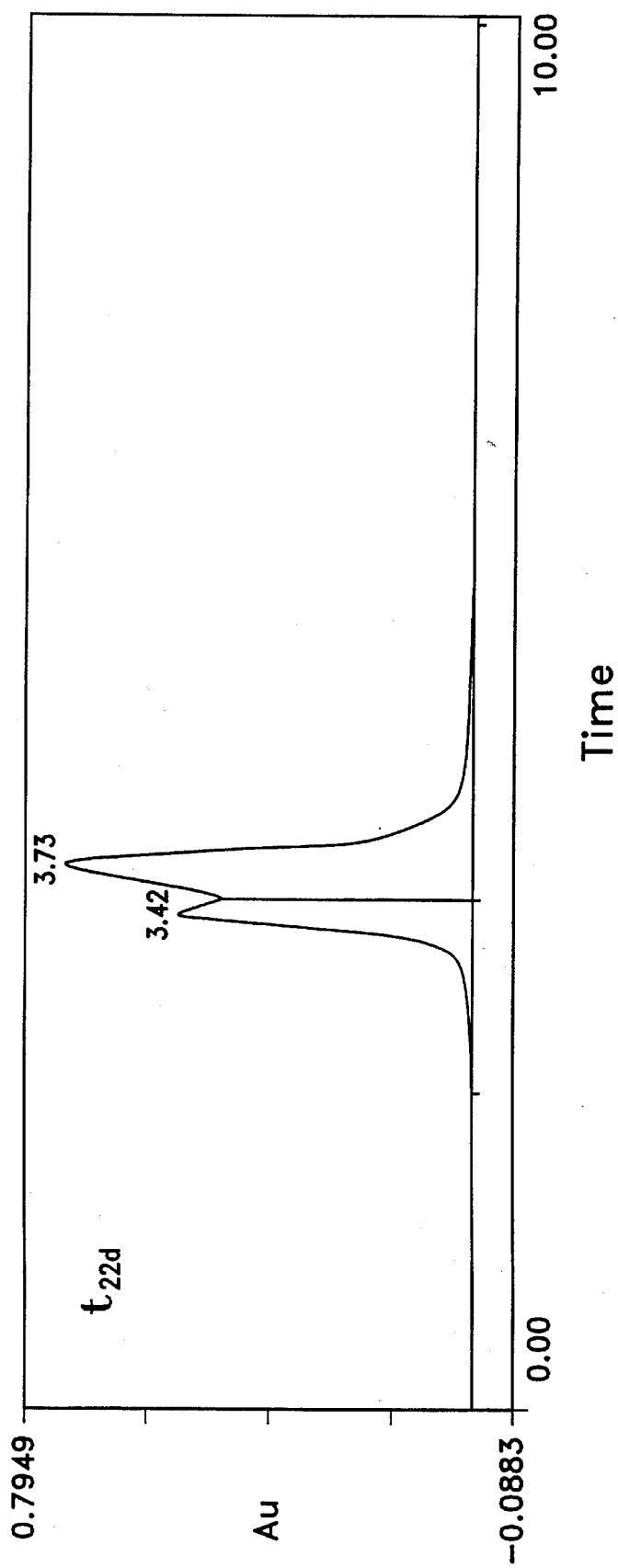
Figure 2A:
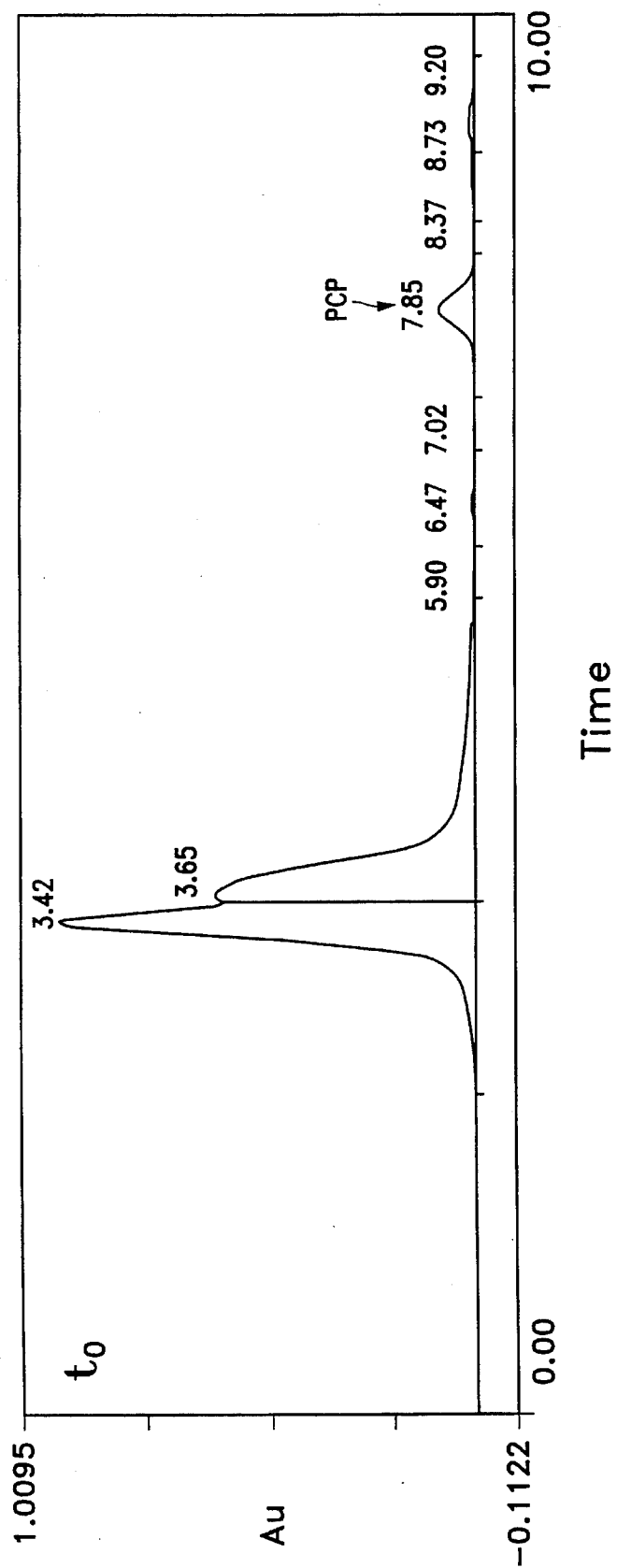
FIGS. 2a and 2b represent the high pressure liquid chromatograms of a contaminated sample of flocked process water at the time of treatment with ATCC 55473 and 22 days later, respectively.
Figure 2B:
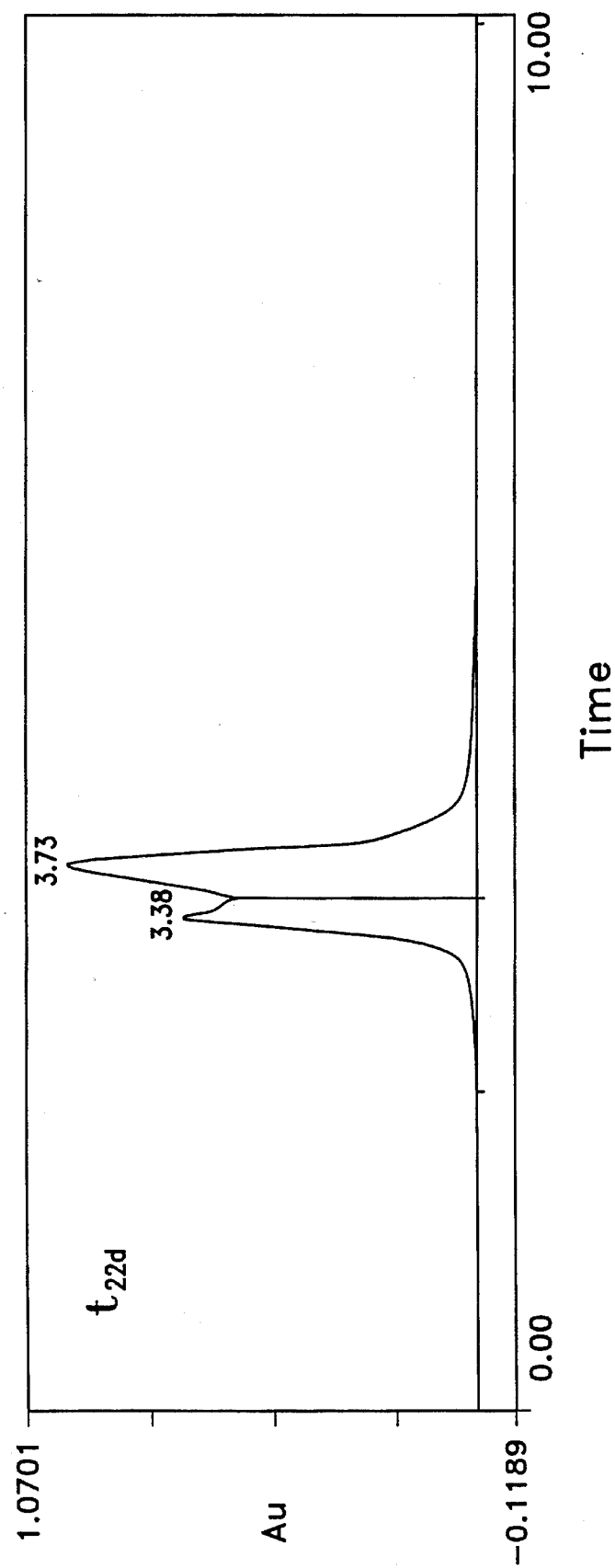

Table VII shows the three aqueous sample types monitored for PCP transformation at specific intervals. Both control and active samples from each source transformed PCP. However, the rate of PCP biotransformation in each sample type was greater in the aliquot that was inoculated with the bacterium than in the non-inoculated control. In the case of the unflocked and flocked process water, PCP was completely removed by day 22 while controls contained residual PCP. Also FIGS. 1a and 1b show the high pressure liquid chromatogram of the contaminant profile of the samples of the unflocked process water on days 0 and 22. FIGS. 2a and 2b show the high pressure liquid chromatograms of the contaminant profile of the samples of the flocked process water on days 0 and 22.

TABLE VII

| Time (days) | MW1 | MW2 | WCM4 |
|---|---|---|---|
| 0 | 592.3 | 240.2 | 136.8 |
| 8 | 185.4/79.2 | 35.6/17.9 | 37.7/20 |
| 13 | 160.1/35.3 | 30.9/0 | 6.1/2.9 |
| 22 | 17.4/0 | 39.3/0 | 0/0 |

MW1: Unflocked process water (pH 5.5)
MW2: Flocked process water (pH 6)
WCM4: Groundwater (pH 6)

The samples were placed in 50-ml serum-stoppered bottles, autoclaved 20 minutes and degassed with $N_2$. To each sample was added 0.5% DL-lactic acid (85%). Control samples were analyzed without further treatment. Active samples were inoculated with 1 ml of *A. viscosus dechlorini* actively dechlorinating PCP. The samples were maintained on the benchtop at ~22° C. Samples were taken at specified intervals, filtered through a 0.2 pm filter (Millipore) and analyzed by HPLC as in TABLE II.

We claim:

1. A biologically pure culture of *Actinomyces viscosus* strain ATCC 55473 or mutants thereof capable of degrading pentachlorophenol in aqueous substrates containing yeast extract and lactic acid under anaerobic conditions without production of toxigenic or mutagenic intermediates selected from the group consisting of 2,3,4,5-tetrachlorophenol; 2,3,4-trichlorophenol; 3,4,5-trichlorophenol; 2,4,5-trichlorophenol; 2,4,6-trichlorophenol and 2,3,6-trichlorophenol.

2. A method of biologically degrading pentachlorophenol in an aqueous substrate containing yeast extract and lactic acid without production of toxigenic or mutagenic intermediates selected from the group consisting of 2,3,4,5-tetrachlorophenol; 2,3,4- trichlorophenol; 3,4,5-trichlorophenol; 2,4,5-trichlorophenol; 2,4,6-trichlorophenol and 2,3,6-trichlorophenol under anaerobic conditions comprising inoculating said substrate with a microorganism possessing all the identifying characteristics of *Actinomyces viscosus* strain ATCC 55473 under conditions sufficient for said microorganism to degrade said pentachlorophenol without producing said intermediates.

* * * * *